United States Patent [19]

Chu

[11] 3,965,210

[45] June 22, 1976

[54] SELECTIVE PRODUCTION OF PARA-XYLENE AND CATALYST THEREFOR

[75] Inventor: Chin-Chiun Chu, South Plainfield, N.J.

[73] Assignee: Mobil Oil Corporation, New York, N.Y.

[22] Filed: Jan. 6, 1975

[21] Appl. No.: 538,667

[52] U.S. Cl. ............................ 260/671 M; 252/430; 242/455 Z; 260/671 C; 260/671 R; 208/DIG. 2
[51] Int. Cl.² ........................ C07C 3/52; C07C 15/08
[58] Field of Search ....... 260/671 R, 671 C, 671 M; 252/430, 455 Z; 208/DIG. 2

[56] References Cited
UNITED STATES PATENTS

| | | | |
|---|---|---|---|
| 3,036,980 | 5/1962 | Dunham et al. | 252/455 |
| 3,254,034 | 5/1966 | Dwyer et al. | 252/430 |
| 3,277,018 | 10/1966 | Plank et al. | 260/671 |
| 3,398,177 | 8/1968 | Stewart | 252/455 |
| 3,484,428 | 12/1969 | Kallenbach | 252/430 |
| 3,682,996 | 8/1972 | Kerr | 252/455 |
| 3,725,302 | 4/1973 | Shively et al. | 252/455 |
| 3,751,506 | 8/1973 | Burress | 260/671 |

*Primary Examiner*—Delbert E. Gantz
*Assistant Examiner*—C. E. Spresser
*Attorney, Agent, or Firm*—Charles A. Huggett; Raymond W. Barclay

[57] ABSTRACT

Catalyst of a crystalline aluminosilicate zeolite, said zeolite having a silica to alumina ratio of at least about 12 and a constraint index, as hereinafter defined, within the approximate range of 1 to 12, the surface of which catalyst has been modified by contact with a polymer made up of meta-carborane units connected by siloxane units and process for the selective production of para-xylene by methylation of toluene in the presence of said catalyst.

15 Claims, No Drawings

SELECTIVE PRODUCTION OF PARA-XYLENE AND CATALYST THEREFOR

BACKGROUND OF THE INVENTION

1. Field of the Invention

This invention relates to a modified crystalline aluminosilicate catalyst and to a process for the selective production of para-xylene by methylation of toluene utilizing such catalyst.

2. Description of the Prior Art

Alkylation of aromatic hydrocarbons utilizing crystalline aluminosilicate catalysts has heretofore been described. U.S. Pat. No. 2,904,607 to Mattox refers to alkylation of aromatic hydrocarbons with an olefin in the presence of a crystalline metallic aluminosilicate having uniform pore openings of about 6 to 15 Angstrom units. U.S. Pat. No. 3,251,897 to Wise describes alkylation of aromatic hydrocarbons in the presence of X- or Y-type crystalline aluminosilicate zeolites, specifically such type zeolites wherein the cation is rare earth and/or hydrogen. U.S. Pat. No. 3,751,504 to Keown et al. and U.S. Pat. No. 3,751,506 to Burress describe vapor phase alkylation of aromatic hydrocarbons with olefins, e.g. benzene with ethylene, in the presence of a ZSM-5 type zeolite catalyst.

The alkylation of toluene with methanol in the presence of a cation exchanged zeolite Y has been described by Yashima et al. in the Journal of Catalysis 16, 273–280 (1970). These workers reported selective production of paraxylene over the approximate temperature range of 200° to 275°C., with the maximum yield of para-xylene in the mixture of xylenes, i.e. about 50 percent of the xylene product mixture being observed at 225°C. Higher temperatures were reported to result in an increase in the yield of meta-xylene and a decrease in production of para and ortho-xylenes.

Crystalline aluminosilicate zeolites, modified by reaction with an organic substituted silane, have been described in U.S. Pat. No. 3,682,996 to Kerr and in U.S. Pat. No. 3,698,157 to Allen et al. The former of these patents describes, as novel compositions of matter, crystalline aluminosilicate esters made by reacting a crystalline aluminosilicate having an available hydrogen atom with an organic silane having a SiH group. The resulting compositions were disclosed as being catalysts useful for hydrocarbon processes, particularly hydrocracking. In the latter of the above patents, the use of ZSM-5 type crystalline aluminosilicate zeolites modified by treatment with an organic-radical substituted silane are described, together with the use of such modified zeolites in chromatographic separation of the compounds contained in a $C_8$ aromatic feed stock.

While the above-noted prior art is considered of interest in connection with the subject matter of the present invention, the catalyst described herein, the surface of which is modified by contact with a polymer made up of meta-carborane units connected by siloxane units and the use of such catalyst in selective methylation of toluene to para-xylene has not, insofar as is known, been heretofore described.

Of the xylene isomers, i.e. ortho-, meta- and para-xylene, the latter is of particular value being useful in the manufacture of terephthalic acid which is an intermediate in the manufacture of synthetic fibers such as "Dacron." Mixtures of xylene isomers either alone or in further admixture with ethylbenzene, generally containing a concentration of about 24 weight percent para-xylene in the equilibrium mixture, have been previously separated by expensive superfraction and multistage refrigeration steps. Such processes, as will be realized, has involved high operation costs and has a limited yield.

SUMMARY OF THE INVENTION

In accordance with the present invention, there has been discovered a modified crystalline aluminosilicate zeolite having a silica to alumina ratio of at least about 12 and a constraint index, as hereinafter defined, of from about 1 to about 12, which has been modified by contact with a polymer made up of meta-carborane units connected by siloxane units. The invention is also directed to a process for selectively producing para-xylene in preference to meta- or ortho-xylene by reaction of toluene with a methylating agent in the presence of such catalyst.

Compared to a conventional thermodynamic equilibrium xylene mixture in which the para:meta:ortho ratio is approximately 1:2:1, the process described herein affords a xylene product having a para:meta:ortho ratio of about 46:3:1. The improved para-xylene yield reduces the cost of production and most important the cost of separation of para-xylene from its isomers, which is the most expensive step in the current method employed for producing para-xylene.

The present process comprises methylation of toluene, preferably by reaction of the latter with methanol, in the presence of a particular modified crystalline aluminosilicate zeolite catalyst. The catalyst employed is a crystalline aluminosilicate zeolite having a silica to alumina ratio of at least about 12 and a constraint index within the approximate range of 1 to 12, modified by surface reaction with a polymer made up of meta-carbone units connected by siloxane units. The size of the specified polymer is sufficiently large as to be unable to penetrate the zeolite pore structure. A particularly preferred method of surface modification involves reaction of the zeolite with the specified polymer followed by calcination.

The zeolite catalysts herein described are members of a novel class of zeolites exhibiting some unusual properties. These catalysts induce profound transformations of aliphatic hydrocarbons to aromatic hydrocarbons in commercially desirable yields and are generally highly effective in conversion reactions involving aromatic hydrocarbons. Although they have unusually low alumina contents, i.e. high silica to alumina ratios, they are very active even when the silica to alumina ratio exceeds 30. The activity is surprising since catalytic activity is generally attributed to framework aluminum atoms and cations associated with these aluminum atoms. These catalysts retain their crystallinity for long periods in spite of the presence of steam at high temperature which induces irreversible collapse of the framework of other zeolites, e.g. of the X and A type. Furthermore, carbonaceous deposits, when formed, may be removed by burning at higher than usual temperatures to restore activity. In many environments the zeolites of this class exhibit very low coke forming capability, conducive to very long times on stream between burning regenerations.

An important characteristic of the crystal structure of this class of zeolites is that it provides constrained access to, and egress from the intracrystalline free space by virtue of having a pore dimension greater than about 5 Angstroms and pore windows of about a size such as would be provided by 10-membered rings of oxygen atoms. It is to be understood, of course, that these rings are those formed by the regular disposition of the tetrahedra making up the anionic framework of the crystalline aluminosilicate, the oxygen atoms themselves being bonded to the silicon or aluminum atoms at the centers of the tetrahedra. Briefly, the preferred type of catalysts useful in this invention possess, in combination: a silica to alumina ratio of at least about 12; and a structure providing constrained access to the crystalline free space.

The silica to alumina ratio referred to may be determined by conventional analysis. This ratio is meant to represent, as closely as possible, the ratio in the rigid anionic framework of the zeolite crystal and to exclude aluminum in the binder or in cationic or other form within the channels. Although catalysts with a silica to alumina ratio of at least 12 are useful, it is preferred to use catalysts having higher ratios of at least about 30. Such catalysts, after activation, acquire an intracrystalline sorption capacity for normal hexane which is greater than that for water, i.e. they exhibit "hydrophobic" properties. It is believed that this hydrophobic character is advantageous in the present invention.

The type zeolites useful in this invention freely sorb normal hexane and have a pore dimension greater than about 5 Angstroms. In addition, the structure must provide constrained access to larger molecules. It is sometimes possible to judge from a known crystal structure whether such constrained access exists. For example, if the only pore windows in a crystal are formed by 8-membered rings of oxygen atoms, then access by molecules of large cross-section than normal hexane is excluded and the zeolite is not of the desired type. Windows of 10-membered rings are preferred, although, in some instances, excessive puckering or pore blockage may render these catalysts ineffective. Twelve-membered rings do not generally appear to offer sufficient constraint to produce the advantageous conversions, although puckered structures exist such as TMA offretite which is a known effective zeolite. Also, structures can be conceived, due to pore blockage or other cause, that may be operative.

Rather than attempt to judge from crystal structure whether or not a catalyst possesses the necessary constrained access, a simmple determination of the "constraint index" may be made by passing continuously a mixture of an equal weight of normal hexane and 3-methylpentane over a small sample, approximately 1 gram or less, of catalyst at atmospheric pressure according to the following procedure. A sample of the catalyst, in the form of pellets or extrudate, is crushed to a particle size about that of coarse sand and mounted in a glass tube. Prior to testing, the catalyst is treated with a stream of air at 1000°F. for at least 15 minutes. The catalyst is then flushed with helium and the temperature adjusted between 550°F. and 950°F. to give an overall conversion between 10% and 60%. The mixture of hydrocarbons is passed at 1 liquid hourly space velocity (i.e., 1 volume of liquid hydrocarbon per volume of catalyst per hour) over the catalyst with a helium dilution to give a helium to total hydrocarbon mole ratio of 4:1. After 20 minutes on stream, a sample of the effluent is taken and analyzed, most conveniently by gas chromatography, to determine the fraction remaining unchanged for each of the two hydrocarbons.

The "constraint index" is calculated as follows:

$$\text{Constraint Index} = \frac{\log_{10} (\text{fraction of n-hexane remaining})}{\log_{10} (\text{fraction of 3-methylpentane remaining})}$$

The constraint index approximates the ratio of the cracking rate constants for the two hydrocarbons. Catalysts suitable for the present invention are those having a constraint index in the approximate range of 1 to 12. Constraint Index (CI) values for some typical catalysts are:

| CAS | C.I. |
|---|---|
| ZSM-5 | 8.3 |
| ZSM-11 | 8.7 |
| ZSM-12 | 2 |
| ZSM-21 | 4.5 |
| ZSM-35 | 4.5 |
| TMA Offretite | 3.7 |
| Beta | 0.6 |
| ZSM-4 | 0.5 |
| H-Zeolon | 0.5 |
| REY | 0.4 |
| Amorphous Silica-Alumina | 0.6 |
| Erionite | 38 |

It is to be realized that the above constraint index values typically characterize the specified zeolites but that such are the cumulative result of several variables used in determination and calculation thereof. Thus, for a given zeolite depending on the temperature employed within the aforenoted range of 550°F. to 950°F., with accompanying conversion between 10% and 60%, the constraint index may vary within the indicated approximate range of 1 to 12. Likewise, other variables such as the crystal size of the zeolite, the presence of possibly occluded contaminants and binders intimately combined with the zeolite may affect the constraint index. It will accordingly be understood by those skilled in the art that the constraint index, as utilized herein, while affording a highly useful means for characterizing the zeolites of interest is approximate, taking into consideration the manner of its determination, with the probability, in some instances, of compounding variable extremes. However, in all instances, at a temperature within the above-specified range of 550°F. to 950°F., the constraint index will have a value for any given zeolite of interest herein within the approximate range of 1 to 12.

The class of zeolites defined herein is exemplified by ZSM-5, ZSM-11, ZSM-12, ZSM-21, ZSM-35 and other similar materials. Recently issued U.S. Pat. No. 3,702,886 describing and claiming ZSM-5 is incorporated herein by reference.

ZSM-11 is more particularly described in U.S. Pat. No. 3,709,979, the entire contents of which are incorporated herein by reference.

ZSM-12 is more particularly described in U.S. Pat. No. 3,832,449, the entire contents of which are incorporated herein by reference.

ZSM-21 is more particularly described in U.S. application Ser. No. 560,412, filed Mar. 20, 1975. This zeolite can be identified, in terms of mole ratios of oxides and in the anhydrous state, as follows:

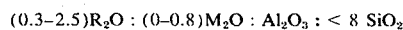

wherein R is an organic nitrogen-containing cation derived from a 2-(hydroxyalkyl) trialkylammonium compound and M is an alkali metal cation, and is characterized by a specified X-ray powder diffraction pattern.

In a preferred synthesized form, the zeolite has a formula, in terms of mole ratios of oxides and in the anhydrous state, as follows:

(0.4–2.5)R$_2$O : (0–0.6) M$_2$O : Al$_2$O$_3$ : xSiO$_2$ wherein R is an organic nitrogen-containing cation derived from a 2-(hydroxyalkyl)trialkylammonium compound, wherein alkyl is methyl, ethyl or a combination thereof, M is an alkali metal, especially sodium, and x is from greater than 8 to about 50.

The synthetic ZSM-21 zeolite possesses a definite distinguishing crystalline structure whose X-ray diffraction pattern shows substantially the significant lines set forth in Table I. It is observed that this X-ray diffraction pattern (significant lines) is similar to that of natural ferrierite with a notable exception being that natural ferrierite patterns exhibit a significant line at 11.33A.

TABLE I

| d(A) | I/Io |
|---|---|
| 9.8 ± 0.20 | Strong |
| 9.1 ± 0.19 | Medium |
| 8.0 ± 0.16 | Weak |
| 7.1 ± 0.14 | Medium |
| 6.7 ± 0.14 | Medium |
| 6.0 ± 0.12 | Weak |
| 4.37 ± 0.09 | Weak |
| 4.23 ± 0.09 | Weak |
| 4.01 ± 0.08 | Very Strong |
| 3.81 ± 0.08 | Very Strong |
| 3.69 ± 0.07 | Medium |
| 3.57 ± 0.07 | Very Strong |
| 3.51 ± 0.07 | Very Strong |
| 3.34 ± 0.07 | Medium |
| 3.17 ± 0.06 | Strong |
| 3.08 ± 0.06 | Medium |
| 3.00 ± 0.06 | Weak |
| 2.92 ± 0.06 | Medium |
| 2.73 ± 0.06 | Weak |
| 2.66 ± 0.05 | Weak |
| 2.60 ± 0.05 | Weak |
| 2.49 ± 0.05 | Weak |

A further characteristic of ZSM-21 is its sorptive capacity providing said zeolite to have increased capacity for 2-methylpentane (with respect to n-hexane soprtion by the ratio n-hexane/2-methyl-pentane) when compared with a hydrogen form of natural ferrierite resulting from calcination of an ammonium exchanged form. The characteristic sorption ratio n-hexane/2-methylpentane for ZSM-21 (after calcination at 600°C.) is less than 10, whereas that ratio for the natural ferrierite is substantially greater than 10, for example, as high as 34 or higher.

Zeolite ZSM-21 can be suitably prepared by preparing a solution containing sources of an alkali metal oxide, preferably sodium oxide, an organic nitrogen-containing oxide, an oxide of aluminum, an oxide of silicon and water and having a composition, in terms of mole ratios of oxides, falling within the following ranges:

| R+ | Broad | Preferred |
|---|---|---|
| R++M+ | 0.2–1.0 | 0.3–0.9 |
| OH$^-$/SiO$_2$ | 0.05–0.5 | 0.07–0.49 |
| H$_2$O/OH$^-$ | 41–500 | 100–250 |
| SiO$_2$/Al$_2$O$_3$ | 8.8–200 | 12–60 | wherein R is an organic nitrogen-containing cation derived from a 2-(hydroxyalkyl) trialkylammonium compound and M is an alkali metal ion, and maintaining the mixture until crystals of the zeolite are formed. (The quantity of OH$^-$ is calculated only from the inorganic sources of alkali without any organic base contribution). Thereafter, the crystals are separated from the liquid and recovered. Typical reaction conditions consist of heating the foregoing reaction mixture to a temperature of from about 90°C. to about 400°C. for a period of time of from about 6 hours to about 100 days. A more preferred temperature range is from about 150°C. to about 400°C. with the amount of time at a temperature in such range being from about 6 hours to about 80 days.

The digestion of the gel particles is carried out until crystals form. The solid product is separated from the reaction medium, as by cooling the whole to room temperature, filtering and water washing. The crystalline product is thereafter dried, e.g. at 230°F. for from about 8 to 24 hours.

ZSM-35 is more particularly described in U.S. application Ser. No. 528,061, filed Nov. 29, 1974. This zeolite can be identified, in terms of mole ratios of oxides and in the anhydrous state, as follows:

(0.3–2.5)R$_2$O : (0–0.8)M$_2$O : Al$_2$O$_3$ : < 8 SiO$_2$ wherein R is an organic nitrogen-containing cation derived from ethylenediamine or pyrrolidine and M is an alkali metal cation, and is characterized by a specified X-ray powder diffraction pattern.

In a preferred synthesized form, the zeolite has a formula, in terms of mole ratios of oxides and in the anhydrous state, as follows:

(0.4–2.5)R$_2$O : (0.0.6)M$_2$O : Al$_2$O$_3$ : xSiO$_2$ wherein R is an organic nitrogen-containing cation derived from ethylenediamine or pyrrolidine, M is an alkali metal, especially sodium, and x is from greater than 8 to about 50.

The synthetic ZSM-35 zeolite possesses a definite distinguishing crystalline structure whose X-ray diffraction pattern shows substantially the significant lines set forth in Table II. It is observed that this X-ray diffraction pattern (with respect to significant lines) is similar to that of natural ferrierite with a notable exception being that natural ferrierite patterns exhibit a significant line at 11.33A. Close examination of some individual samples of ZSM-35 may show a very weak line at 11.3–11.5A. This very weak line, however, is determined not to be a significant line for ZSM-35.

TABLE II

| d(A) | I/Io |
|---|---|
| 9.6 ± 0.20 | Very Strong – Very Very Strong |
| 7.10 ± 0.15 | Medium |
| 6.98 ± 0.14 | Medium |
| 6.64 ± 0.14 | Medium |
| 5.78 ± 0.12 | Weak |
| 5.68 ± 0.12 | Weak |
| 4.97 ± 0.10 | Weak |
| 4.58 ± 0.09 | Weak |
| 3.99 ± 0.08 | Strong |
| 3.94 ± 0.08 | Medium Strong |
| 3.85 ± 0.08 | Medium |
| 3.78 ± 0.08 | Strong |
| 3.74 ± 0.08 | Weak |
| 3.66 ± 0.07 | Medium |
| 3.54 ± 0.07 | Very Strong |
| 3.48 ± 0.07 | Very Strong |
| 3.39 ± 0.07 | Weak |
| 3.32 ± 0.07 | Weak Medium |
| 3.14 ± 0.06 | Weak Medium |
| 2.90 ± 0.06 | Weak |
| 2.85 ± 0.06 | Weak |

TABLE II-continued

| d(A) | I/Io |
|---|---|
| 2.71 ± 0.05 | Weak |
| 2.65 ± 0.05 | Weak |
| 2.62 ± 0.05 | Weak |
| 2.58 ± 0.05 | Weak |
| 2.54 ± 0.05 | Weak |
| 2.48 ± 0.05 | Weak |

A further characteristic of ZSM-35 is its sorptive capacity proving said zeolite to have increased capacity for 2-methylpentane (with respect to n-hexane sorption by the ratio n-hexane/2-methylpentane) when compared with a hydrogen form of natural ferrierite resulting from calcination of an ammonium exchanged form. The characteristic sorption ratio n-hexane/2-methylpentane for ZSM-35 (after calcination at 600°C.) is less than 10, whereas that ratio for the natural ferrierite is substantially greater than 10, for example, as high as 34 or higher.

Zeolite ZSM-35 can be suitably prepared by preparing a solution containing sources of an alkali metal oxide, preferably sodium oxide, an organic nitrogen-containing oxide, an oxide of aluminum, an oxide of silicon and water and having a composition, in terms of mole ratios of oxides, falling within the following ranges:

| R+ | Broad | Preferred |
|---|---|---|
| R+ + M+ | 0.2–1.0 | 0.3–0.9 |
| OH−/SiO₂ | 0.05–0.5 | 0.07–0.49 |
| H₂O/OH− | 41–500 | 100–250 |
| SiO₂/Al₂O₃ | 8.8–200 | 12–60 | wherein R is an organic nitrogen-containing cation derived from pyrrolidine or ethylenediamine and M is an alkali metal ion, and maintaining the mixture until crystals of the zeolite are formed. (The quantity of OH− is calculated only from the inorganic sources of alkali without any organic base contribution). Thereafter, the crystals are separated from the liquid and recovered. Typical reaction conditions consist of heating the foregoing reaction mixture to a temperature of from about 90°C. to about 400°C. for a period of time of from about 6 hours to about 100 days. A more preferred temperature range is from about 150°C. to about 400°C. with the amount of time at a temperature in such range being from about 6 hours to about 80 days.

The digestion of the gel particles is carried out until crystals form. The solid product is separated from the reaction medium, as by cooling the whole to room temperature, filtering and water washing. The crystalline product is dried, e.g. at 230°F., for from about 8 to 24 hours.

The specific zeolites described, when prepared in the presence of organic cations, are catalytically inactive, possibly because the intracrystalline free space is occupied by organic cations from the forming solution. They may be activated by heating in an inert atmosphere at 1000°F. for one hour, for example, followed by base exchange with ammonium salts followed by calcination at 1000°F. in air. The presence of organic cations in the forming solution may not be absolutely essential to the formation of this type zeolite; however, the presence of these cations does appear to favor the formation of this special type of zeolite. More generally, it is desirable to activate this type catalyst by base exchange with ammonium salts followed by calcination in air at about 1000°F. for from about 15 minutes to about 24 hours.

Natural zeolites may sometimes be converted to this type zeolite catalyst by various activation procedures and other treatments such as base exchange, steaming, alumina extraction and calcination, in combinations. Natural minerals which may be so treated include ferrierite, brewsterite, stilbite, dachiardite, epistilbite, heulandite and clinoptilolite. The preferred crystalline aluminosilicates are ZSM-5, ZSM-11, ZSM-12, ZSM-21 and ZSM-35, with ZSM-5 particularly preferred.

The catalysts of this invention may be in the hydrogen form or they may be base exchanged or impregnated to contain ammonium or a metal cation complement. It is desirable to calcine the catalyst after base exchange. The metal cations that may be present include any of the cations of the metals of Groups I through VIII of the periodic table. However, in the case of Group IA metals, the cation content should in no case be so large as to effectively inactivate the catalyst.

In a preferred aspect of this invention, the catalysts hereof are selected as those having a crystal framework density, in the dry hydrogen form, of not substantially below about 1.6 grams per cubic centimeter. It has been found that zeolites which satisfy all three of these criteria are most desired because they tend to maximize the production of gasoline boiling range hydrocarbon products. Therefore, the preferred catalysts of this invention are those having a constraint index as defined above of about 1 to about 12, a silica to alumina ratio of at least about 12 and a dried crystal density of not less than about 1.6 grams per cubic centimeter. The dry density for known structures may be calculated from the number of silicon plus aluminum atoms per 1000 cubic Angstroms, as given, e.g., on page 19 of the article on Zeolite Structure by W. M. Meir. This paper, the entire contents of which are incorporated herein by reference, is included in "Proceedings of the Conference on Molecular Sieves, London, April 1967", published by the Society of Chemical Industry, London, 1968. When the crystal structure is unknown, the crystal framework density may be determined by classical pyknometer techniques. For example, it may be determined by immersing the dry hydrogen form of the zeolite in an organic solvent which is not sorbed by the crystal. It is possible that the unusual sustained activity and stability of this class of zeolites is associated with its high crystal anionic framework density of not less than about 1.6 grams per cubic centimeter. This high density, of course, must be associated with a relatively small amount of free space within the crystal, which might be expected to result in more stable structures. This free space, however, is important as the locus of catalytic activity.

Crystal framework densities of some typical zeolites are:

| Zeolite | Void Volume | Framework Density |
|---|---|---|
| Ferrierite | 0.28 cc/cc | 1.76 g/cc |
| Mordenite | .28 | 1.7 |
| ZSM-5, -11 | .29 | 1.79 |
| Dachiardite | .32 | 1.72 |
| L | .32 | 1.61 |
| Clinoptilolite | .34 | 1.71 |
| Laumontite | .34 | 1.77 |
| ZSM-4 (Omega) | .38 | 1.65 |
| Heulandite | .39 | 1.69 |

| Zeolite | Void Volume | Framework Density |
|---|---|---|
| P | .41 | 1.57 |
| Offretite | .40 | 1.55 |
| Levynite | .40 | 1.54 |
| Erionite | .35 | 1.51 |
| Gmelinite | .44 | 1.46 |
| Chabazite | .47 | 1.45 |
| A | .5 | 1.3 |
| Y | .48 | 1.27 |

The zeolite is converted from its as synthesized alkali metal form to the hydrogen form, generally by intermediate formation of the ammonium form as a result of ammonium ion exchange and calcination of the ammonium form to yield the hydrogen form. In addition to the hydrogen form, other forms of the zeolite wherein the original alkali metal has been reduced to less than about 1.5 percent by weight may be used. Thus, the original alkali metal of the zeolite may be replaced by ion exchange with other suitable ions of Groups I-B to VIII of the Periodic Table including, by way of example, nickel, zinc or rare earth metals.

The crystals of zeolite in a form substantially free of alkali metal, i.e., containing less than about 1.5 weight percent alkali metal, are then contacted with a polymer made up of meta-carborane units connected by siloxane units. Representative of such compounds are the commercially available Dexsil type materials. Particularly feasible polymers are the products known as Dexsil 300 GC, Dexsil 400 GC and Dexsil 410 GC marketed by Analabs having the structural formulae:

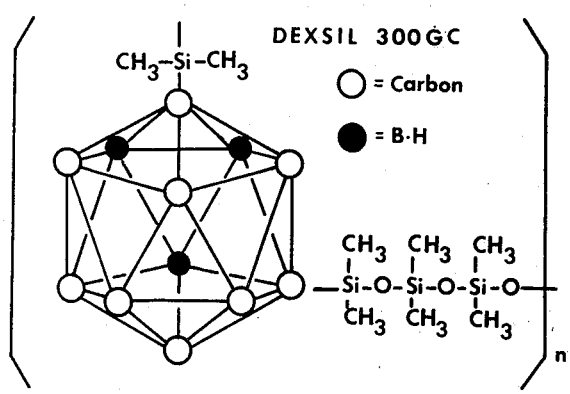

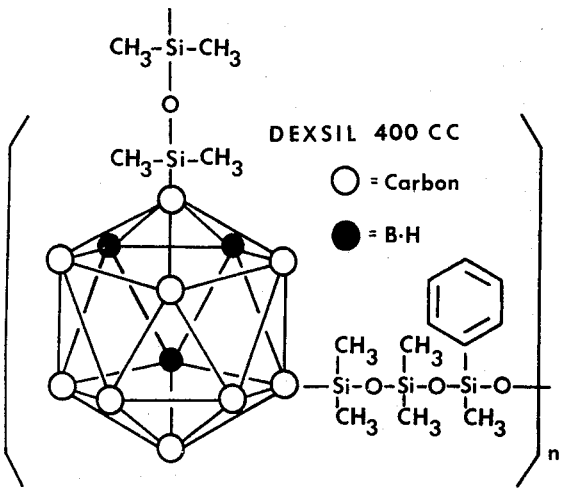

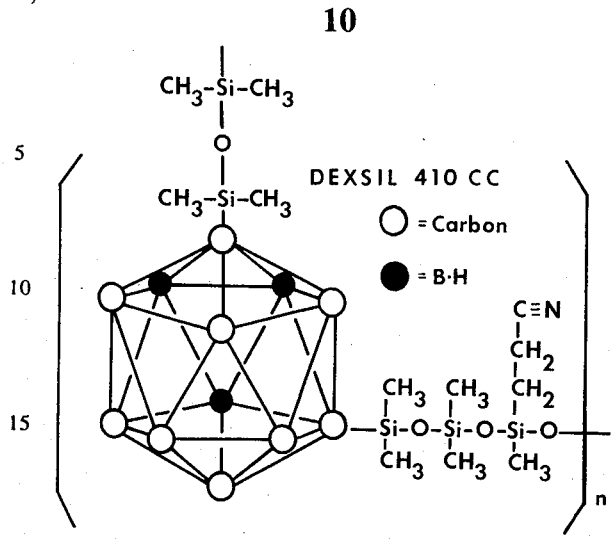

where $n$ is a number from 21 to 47 providing a product having a molecular weight between about 9000 and about 20000.

Contact of the zeolite with the above-specified polymer is generally carried out in the presence of an organic solvent. Thus, the polymer is dissolved in a solvent such as chloroform to form an approximately 2–10 weight percent solution. To the solution is then added the desired amount of zeolite. The mixture may be allowed to stand at room temperature with occasional mixing or may be refluxed for several hours, e.g. 1–16 hours. The organic solvent is then removed either by distillation or with a stream of nitrogen or air followed by drying under vacuum. Generally, the boron-silicon containing polymer and zeolite are contacted on a weight basis of about 2 to about 200 percent of zeolite and preferably about 10 to about 100 percent respectively. The amount of the specified polymer should desirably be such as to achieve about 5 to about 50 weight percent of the polymer bonded to the outer surface of the zeolite. It is also preferable that a binder for the zeolite be employed such as, for example, bentonite. For good contact between reactants it is also preferable to employ a reaction medium. Satisfactory reaction media include ethers, aliphatic hydrocarbons and halosubstituted aliphatic hydrocarbons of from 5 to about 8 carbon atoms, aromatic, and halo-substituted aromatic hydrocarbons. A particularly preferred medium is chloroform.

A temperature between about 25°C. and about 150°C. should be employed for the reaction. Usually, the reactants are charged to the medium and heated at the reflux point of the system for about 1 to 16 hours. The mixture is then evaporated to dryness under vacuum and dried in an oven at 110°C. to 150°C. for 3 to 16 hours.

Prior to use the resulting modified zeolite may be calcined in an inert atmosphere, e.g. nitrogen or in an oxygen-containing atmosphere, e.g., air. Calcination takes place at a temperature in the approximate range of 300° to 500°C. and preferably between about 400° and about 450°C.

In practicing the desired methylation process it may be desirable to incorporated the modified zeolite in another material resistant to the temperatures and other conditions employed in the methylation process. Such matrix materials include synthetic or naturally occurring substances as well as inorganic materials such as clay, silica and/or metal oxides. The latter may be either naturally occurring or in the form of gelatinous precipitates or gels including mixtures of silica and metal oxides. Naturally occurring clays which can be composited with the modified zeolite include those of the montmorillonite and kaolin families, which families include the sub-bentonites and the kaolins commonly known as Dixie, McNamee-Georgia and Florida clays or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, the modified zeolites employed herein may be composited with a porous matrix material, such as silica-alumina, silica-magnesia, silica-zirconia, silica-thoria, silica-berylia, silica-titania as well as ternary compositions, such as silica-alumina-thoria, silica-alumina-zirconia, silica-alumina-magnesia and silica-magnesia-zirconia. The matrix may be in the form of a cogel. The relative proportions of finely divided modified zeolite and inorganic oxide gel matrix may vary widely with the zeolite content ranging from between about 1 to about 99 percent by weight and more usually in the range of about 5 to about 80 percent by weight of the composite. A particularly suitable combination is one containing about 65 weight percent of the zeolite in 35 weight percent of a relatively inactive alumina matrix.

Methylation of toluene in the presence of the above-described catalyst is effected by contact of the toluene with a methylating agent, preferably methanol, at a temperature between about 300°C. and about 500°C. and preferably between about 400°C. and about 450°C. The reaction generally takes place at atmospheric pressure, but the pressure may be within the approximate range of 1 atmosphere to 1000 psig. A weight hourly space velocity of between about 1 and about 2000 is generally employed. The molar ratio of methylating agent to toluene is usually between about 0.05 and about 5. when methanol is employed as the methylating agent a suitable molar ratio of methanol to toluene has been found to be approximately 0.1-2 moles of methanol per mole of toluene. With the use of other methylating agents, such as methylchloride, methylbromide, dimethylether or dimethylsulfide, the molar ratio of methylating agent to toluene may vary within the aforenoted range. Reaction is suitably accomplished utilizing a weight hourly space velocity of between about 1 and about 2000 and preferably between about 5 and about 1500. The reaction product consisting predominantly of para-xylene, together with comparatively smaller amounts of meta-xylene and ortho-xylene may be separated by any suitable means, such as by passing the same through a water condenser and subsequently passing the organic phase through a column in which chromatographic separation of the xylene isomers is accomplished.

The following examples will serve to illustrate the process of this invention without limiting the same:

EXAMPLE 1

ZSM-5 crystals were obtained using the following reactants:

Silicate Solution 42.2 lb. Q Brand Sodium Silicate ($Na_2O/SiO_2 = 3.3$)
52.8 lb. Water Acid Solution 612 grams Aluminum Sulfate
1600 grams Sulfuric Acid
7190 grams Sodium Chloride
72.2 lb. Water Organics 1290 grams Tri-n-propylamine
1110 grams n-Propylbromide The silicate solution and acid solution were nozzle mixed to form a gelatinous precipitate that was charged to a 30 gallon stirred autoclave. When gelation was complete the organics were added and the temperature raised to 315°F. with agitation. The reaction mixture was held at 315°F. with an agitation rate of 121RPM for 17 hours. The product at this time was analyzed by X-ray diffraction and was reported to be ZSM-5. The product was then washed free of soluble salts and dried. Analysis of the product gave the following in terms of mole ratios:

| | |
|---|---|
| $Al_2O_3$ | 1.0 |
| $SiO_2$ | 74.4 |
| $Na_2O$ | 0.31 |
| N | 2.26 |
| C | 21.9 |

The ZSM-5 so prepared was precalcined in air at 370°C. and thereafter ammonium exchanged by contacting twice with 5N $NH_4Cl$ solution at 100°C. (15 ml. per gram zeolite), once for 16 hours, the second time for 4 hours, filtered, washed free of chloride and air dried.

The resulting ammonium form of ZSM-5 was converted to the hydrogen form by calcination in air at 1°C./minute to 538°C. and then held at 538°C. for 10 hours.

Treatment of the HZSM-5 so obtained was carried out by contact with Dexsil 300 GC (a polymer made up of meta-carborane units connected by siloxane units). To a solution of 1.0 gram Dexsil 300 in 30 ml chloroform was added 5.0 grams of the HZSM-5. The mixture was allowed to stand at room temperature for 2 hours with occasional swirling. The organic medium was removed with a stream of nitrogen with constant swirling and then dried under vacuum.

A 0.5 gram sample of the modifiedd HZSM-5 catalyst was loaded into a reactor and was calcined in air at 450°C. A toluene/methanol mixture characterized by a toluene/methanol ratio of 1.4 was passed over the catalyst at 450°C. utilizing a weight hourly space velocity of 7.4. Alkylation of toluene was 27.5 percent. Xylene formation was 84 weight percent based on toluene conversion and the para:meta:ortho ratio was 92:6:2.

EXAMPLE 2

A toluene/methanol mixture having a toluene/methanol ratio of 1.4 was passed over a 0.5 gram sample of the modified HZSM-5 catalyst described in Example 1 at 450°C. utilizing a weight hourly space velocity of 33. Alkylation of toluene was 7 percent. The para:-meta:ortho xylene ratio was 95:5:2.

EXAMPLE 3

Ten grams of HZSM-5, prepared as in Example 1, were added to a solution of 20 grams of Dexsil 300 GC in 50 milliliters of chloroform and the resulting mixture refluxed for 16 hours. After removal of chloroform by distillation, the residue was dried by heating at 100°–150°C.

A 5 gram sample of the so modified HZSM-5 was used for methylation of toluene in the same manner as described above in Example 1 but utilizing a weight hourly space velocity of 8.6. Alkylation of toluene was 27 percent. Xylene formation was 84 weight percent based on toluene conversion and the para:meta:ortho ratio was 91:7:2.

EXAMPLE 4

ZSM-35 crystals were obtained using the following reactants:

A. Silicate Solution 101.6 g. Q-Brand Silicate (28.8 wt.% $SiO_2$, 8.9 wt.% $Na_2O$)
6.5 g. 50% NaOH solution
59.8 g. $H_2O$

B. Acid Alum Solution 19.4 g. $Al_2(SO_4)_3 \cdot 18H_2O$
4.5 g. $H_2SO_4$
174 g. $H_2O$

C. Ethylenediamine 30.0 g.

These solutions were mixed together adding Solution C to Solution A then adding Solution B and mixing vigorously for 15 minutes. The mixture was charged to a polypropylene jar and sealed. This was held for 62 days at 210°F. in a non-stirred state to allow the product to crystallize.

The solid crystalline product was filtered from the slurry and water washed to remove unreacted soluble components and then dried at 230°F.

X-ray analyses established the material as ZSM-35. Product analysis on dried sample were as follows:

| | |
|---|---|
| N | 3.09 wt. % |
| Na | 0.07 wt. % |
| $Al_2O_3$ | 10.1 wt. % |
| $SiO_2$ | 85.2 wt. % |
| Solids | 88.4 wt. % |

Sorption properties after calcination 16 hours at 1000°F. were:

| | |
|---|---|
| Cyclohexane | 2.2 wt. % |
| n-Hexane | 5.3 wt. % |
| $H_2O$ | 13.9 wt. % |

The surface area was 347 m²/g.

Treatment of the ZSM-35 so obtained is carried out by contact with Dexsil 300 GC as described above in Example 1.

Methylation of toluene was dimethylether using the above modified ZSM-35 is carried out employing a mole ratio of methanol/toluene of 0.5 in the manner described hereinabove. Methylation of toluene is 29 percent. Xylene formation is 86 weight percent based on toluene conversion and the para:meta:ortho ratio is 89:8:3.

EXAMPLE 5

The ammonium form of ZSM-5 crystals prepared according to Example 1 is calcined at about 1000°F. for 16 hours. Three grams of the calcined material is exchanged with 35 ml. of a 0.5N 2.9/1 zinc chloride/ammonium chloride solution at 110°F. for 4 hours. The material is then washed with water and dried in air to yield a catalyst having a zinc concentration of about 0.5 weight percent and a sodium content of about 0.1 weight percent.

Treatment of the ZSM-5 so obtained is carried out by contact with Dexsil 400 GC in the manner described above in Example 1.

Methylation of toluene with methyl chloride is conducted in the presence of the above-modified ZSM-5 catalyst by passing a mole ratio of 1:1 of toluene and gaseous methyl chloride over the catalyst at a pressure of 1 atmosphere and a temperature of about 400°C. Methylation of toluene is 31 percent. Xylene formation is 70 weight percent based on toluene conversion and the para:meta:ortho ratio is 79:13:8.

EXAMPLE 6

A catalyst of HZSM-11 was prepared and treated with Dexsil 300 GC as described hereinabove.

The so modified HZSM-11 was employed as a catalyst for methylating toluene with methanol as described above in Example 1 except that the WHSV was 35 at 450°C. and the toluene/methanol ratio was 1/1 (molar). Methylation of toluene was 20 percent, xylene formation was 87 weight percent based on toluene conversion and the para:meta:ortho ratio is 65:26:9.

It is to be understood that the foregoing description is merely illustrative of preferred embodiments of the invention of which many variations may be made by those skilled in the art within the scope of the following claims without departing from the spirit thereof.

I claim:

1. A process for the selective production of paraxylene which comprises reacting toluene with a methylating agent in the presence of a catalyst of a crystalline alumino-silicate zeolite, said zeolite having a silica to alumina ratio of at least about 12 and a constraint index within the approximate range of 1 to 12, the surface of said catalyst having been modified by contact with a polymer made up of meta-carbonate units connected by siloxane units and of a size sufficiently large as to be unable to penetrate the zeolite pore structure.

2. The process of claim 1 wherein the crystalline aluminosilicate zeolite is ZSM-5.

3. The process of claim 1 wherein the crystalline aluminosilicate zeolite is ZSM-11.

4. The process of claim 1 wherein the crystalline aluminosilicate zeolite is ZSM-21.

5. The process of claim 1 wherein the crystalline aluminosilicate zeolite is ZSM-35.

6. The process of claim 1 wherein said methylating agent is methanol, methylchloride, methylbromide, dimethylether or dimethylsulfide.

7. The process of claim 1 wherein said polymer has a molecular weight of between about 9000 and about 20000.

8. The process of claim 1 wherein the step of reacting toluene with a methylating agent is carried out at a temperature between about 300°C. and about 500°C., a pressure of between about 1 atmosphere and about 1000 psig, a weight space velocity of between about 1 and about 2000, employing a molar ratio methylating agent to toluene of between about 0.05 and about 5.

9. The process of claim 1 wherein said crystalline aluminosilicate zeolite is characterized by a silica/alumina ratio in excess of 30.

10. A catalyst consisting essentially of a crystalline aluminosilicate zeolite having a silica to alumina ratio of at least about 12 and a constraint index within the approximate range of 1 to 12, the surface of which has been modified by contact with a polymer made up of meta-carborane units connected by siloxane units and of a size sufficiently large as to be unable to penetrate the zeolite pore structure.

11. The catalyst of claim 10 wherein said polymer has a molecular weight between about 9000 and about 20000.

12. The catalyst of claim 10 wherein the crystalline aluminosilicate zeolite is ZSM-5.

13. The catalyst of claim 10 wherein the crystalline aluminosilicate zeolite is ZSM-11.

14. The catalyst of claim 10 wherein the crystalline aluminosilicate zeolite is ZSM-21.

15. The catalyst of claim 10 wherein the crystalline aluminosilicate zeolite is ZSM-35.

* * * * *

UNITED STATES PATENT AND TRADEMARK OFFICE
CERTIFICATE OF CORRECTION

PATENT NO. : 3,965,210
DATED : June 22, 1976
INVENTOR(S) : CHIN-CHIUN CHU

It is certified that error appears in the above-identified patent and that said Letters Patent are hereby corrected as shown below:

Column 2, lines 36-37, "meta-carbone" should be --meta-carborane--.

Column 4, line 64, " < " should be -- > --.

Column 6, line 25, " < " should be -- > --.

Column 14, line 46, Claim 1, "meta-carbonate" should be --meta-carborane--.

Signed and Sealed this

Twenty-second Day of March 1977

[SEAL]

Attest:

RUTH C. MASON
*Attesting Officer*

C. MARSHALL DANN
*Commissioner of Patents and Trademarks*